(12) United States Patent
    Kai

(10) Patent No.:  US 12,667,389 B2
(45) Date of Patent:      Jun. 30, 2026

(54) DEVICE FOR SUPPORTING INSEMINATION

(71) Applicant: Ryoko Kai, Long Island City, NY (US)

(72) Inventor:  Ryoko Kai, Long Island City, NY (US)

( * ) Notice:  Subject to any disclaimer, the term of this patent is extended or adjusted under 35 U.S.C. 154(b) by 1059 days.

(21) Appl. No.: 17/834,643

(22) Filed:  Jun. 7, 2022

(65) Prior Publication Data

US 2023/0225764 A1      Jul. 20, 2023

Related U.S. Application Data

(60) Provisional application No. 63/299,948, filed on Jan. 15, 2022.

(51) Int. Cl.
    *A61B 17/00*      (2006.01)
    *A61B 17/43*      (2006.01)
(52) U.S. Cl.
    CPC .................................... *A61B 17/43* (2013.01)
(58) Field of Classification Search
    CPC ...................................................... A61B 17/43
    See application file for complete search history.

(56) References Cited

U.S. PATENT DOCUMENTS

| | | | | |
|---|---|---|---|---|
| 9,585,694 | B2 * | 3/2017 | Rosenberg ............. | A61H 19/50 |
| 2012/0136204 | A1 * | 5/2012 | Hidalgo-Mendoza ...................... | |
| | | | | A61D 19/027 |
| | | | | 600/38 |
| 2014/0107410 | A1 * | 4/2014 | Rosenberg ............. | A61B 17/43 |
| | | | | 600/38 |
| 2014/0200400 | A1 * | 7/2014 | Berman ................. | A61B 17/43 |
| | | | | 600/38 |
| 2015/0142045 | A1 * | 5/2015 | Bacich .................. | A61F 2/0027 |
| | | | | 606/193 |
| 2021/0386456 | A1 * | 12/2021 | Plessala ............. | A61B 10/0012 |

* cited by examiner

*Primary Examiner* — Joel Lamprecht
(74) *Attorney, Agent, or Firm* — Patent 360; Barry Choobin

(57)      ABSTRACT

A device for supporting insemination that includes an elongated tubular body, the body has a proximal portion, a middle portion, and a distal portion, the proximal portion is of an oval shape, the middle portion is of a narrow tubular shape, and the distal portion is configured as a hub to sealably receive a tip of a syringe. The body further has a hollow central channel that extends throughout the length of the elongated tubular body.

12 Claims, 5 Drawing Sheets

100

130

105

110

120

100

130

105

110

120

200

210

220

DEVICE FOR SUPPORTING INSEMINATION

CROSS-REFERENCE TO RELATED APPLICATIONS

This application claims priority from a U.S. Provisional Patent Appl. No. 63/299,948 filed on Jan. 15, 2022, which is incorporated herein by reference in its entirety.

FIELD OF INVENTION

The present invention relates to methods and devices for efficiently inserting body fluids such as semen into the vagina for use in artificial insemination procedures.

BACKGROUND

Artificial insemination refers to a process of introducing sperm into a reproductive system of a female bypassing the natural process to induce pregnancy. The sperms are delivered into the vagina of the female patient. The sperms can be collected from a male patient and delivered through a catheter into the vagina of the female patient. The sperms can optionally be pre-treated to increase the likelihood of inducing pregnancy. Artificial insemination is a medical process prescribed when natural intercourse is not effective due to any reason. However, many couples who are reluctant to have intercourse are also opting for artificial insemination.

For artificial insemination, a catheter is generally used to deliver the semen inside the reproductive cavity of a female patient. In most cases, targeted delivery of semen is essential for inducing pregnancy. A variety of devices are known in the art for the artificial insemination process. However, the known artificial insemination devices have one or more drawbacks, such as being too complex to use and costly. Moreover, with the known artificial insemination devices, the failure rate for inducing the pregnancy is also too high, which requires repeating the already tedious process more than once.

Thus, a need is appreciated for a device to aid insemination process that is devoid of the aforesaid drawbacks of known artificial insemination devices.

SUMMARY OF THE PRESENT INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a device for supporting insemination that is easy to use.

It is another object of the present invention that the device prevents leakage or wastage increasing the chances of getting pregnant.

It is still another object of the present invention that the device is cost-effective.

In one aspect, disclosed is a device to aid in insemination, the device comprises an elongated tubular body that has a proximal portion, a middle portion, and a distal portion, the proximal portion is of an oval shape, the middle portion is of a narrow tubular shape, and the distal portion is configured as a hub to sealably receive a tip of a syringe; and a hollow central channel extends throughout a length of the elongated tubular body, wherein the hollow central channel at one end opens at a tip of the elongated tubular body and another end of the hollow central channel opens at the hub.

In one implementation, the device further comprises a protruding tip at the tip of the elongated tubular body along with the opening of the hollow central channel. The device is semi-rigid and made from silicone. The device further comprises the syringe, wherein the tip of the syringe is configured to be removably coupled to the hub. The tip of the syringe frictionally fits into the hub. The tip of the syringe and the hub have an interlocking fastening mechanism for securing the tip of the syringe into the hub.

In one aspect, disclosed is a method to aid insemination process, the method comprising the steps of providing a device comprising an elongated tubular body that has a proximal portion, a middle portion, and a distal portion, the proximal portion is of an oval shape, the middle portion is of a narrow tubular shape, and the distal portion is configured as a hub to sealably receive a tip of a syringe, and a hollow central channel that extends throughout a length of the elongated tubular body, wherein the hollow central channel at one end opens at a tip of the elongated tubular body and another end of the hollow central channel opens at the hub. The method further includes the steps of coupling the tip of the syringe to the hub; upon coupling, drawing using the syringe, fluid from a container into the channel and a barrel of the syringe; inserting the device into vagina of a patient in need of getting pregnant; and pushing a plunger of the syringe to eject the sperms through the channel.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
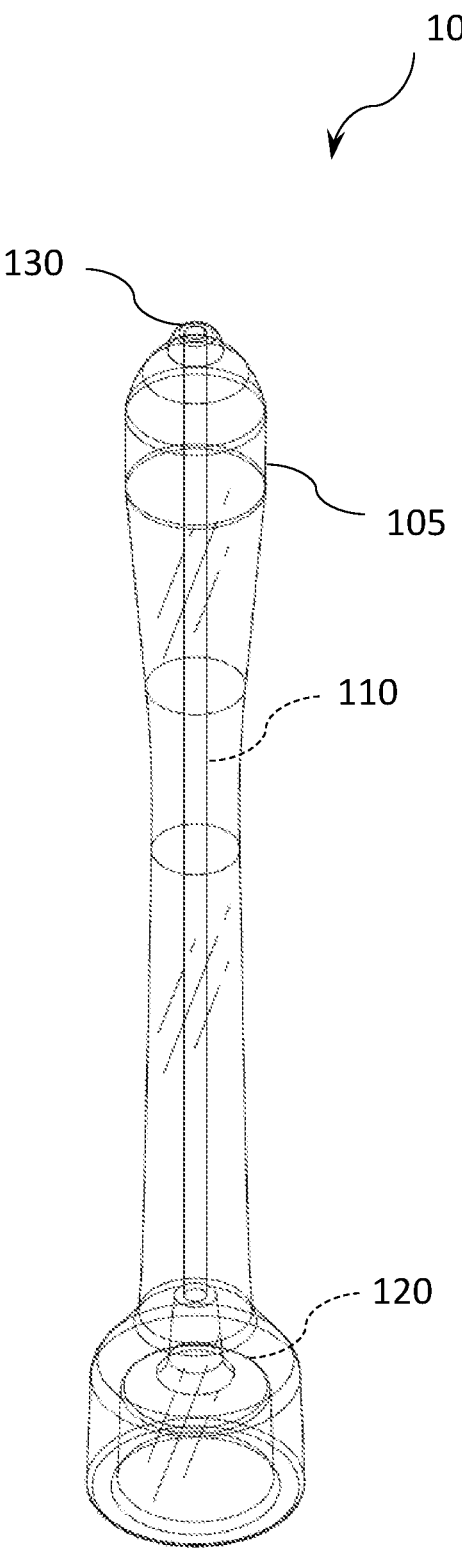
FIG. 1 is a perspective view of a device to aid insemination process, according to an exemplary embodiment of the present invention.
Figure 2:
FIG. 2 is a front view of the device, according to an exemplary embodiment of the present invention.
Figure 2:
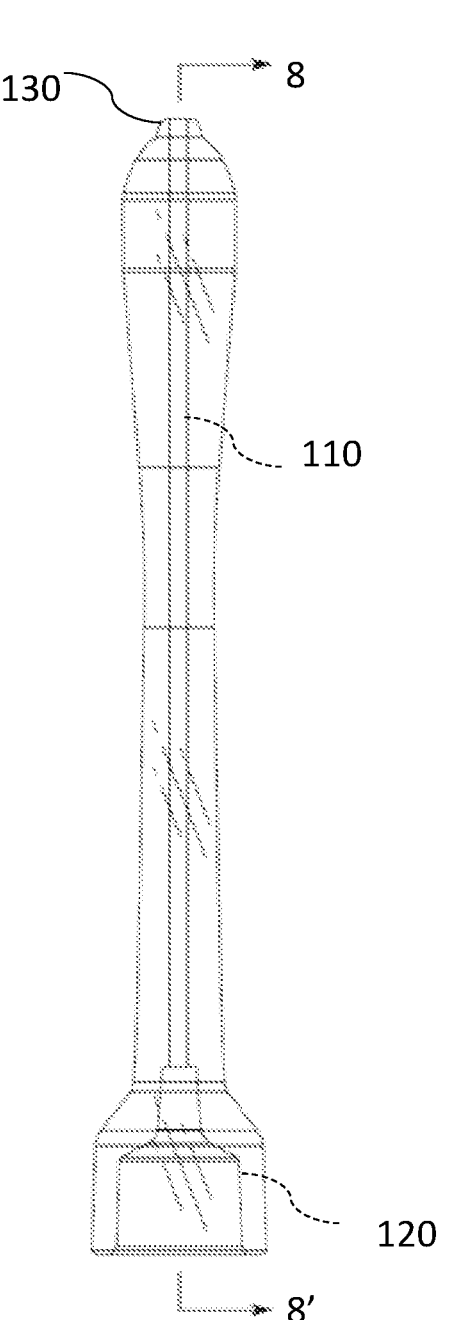

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a device to aid insemination process that makes the process of insemination both easy and efficient. The disclosed device reduces the loss of sperm in the process and thus increases the likelihood of getting pregnant. Referring to FIGS. 1-4 which shows an exemplary embodiment of the disclosed device 100 which is of an elongated tubular geometry. The device 100 includes a body 105 that has a proximal portion, a mid-portion, and a distal portion. The proximal portion is of an oval shape, the middle portion is of a narrow tubular shape, and the distal portion is configured to receive a tip of a syringe. A central hollow channel 110 extends from the tip to the bottom of the body 105. Through channel 110, fluid can be sucked in and ejected out. The channel 110 is open at both ends for the fluid to pass through.

The oval shape of the proximal portion of device 100 can make the insertion of device 100 into the vagina easier and more effective. The narrow and tubular middle portion makes the handling and maneuvering of the device 100 easier and more stable. The oval proximal portion and the other gage parts are gently thinned, so the area of the device that hits the vaginal wall is minimized and the feeling of oppression during insertion can be significantly reduced.

The distal portion of the device 100 can have a hub 120 that can sealably receive a tip of a syringe. The hub can be adapted for different shapes of the tips of syringes, and thus the device 100 can be made for different syringes. Upon coupling the syringe to the device, the inner volume of a syringe can be in fluid communication with the channel 110 of the device 100, such that fluid can be sucked into the syringe through the channel, and the fluid in the syringe can be ejected out through the channel.

Figure 3:
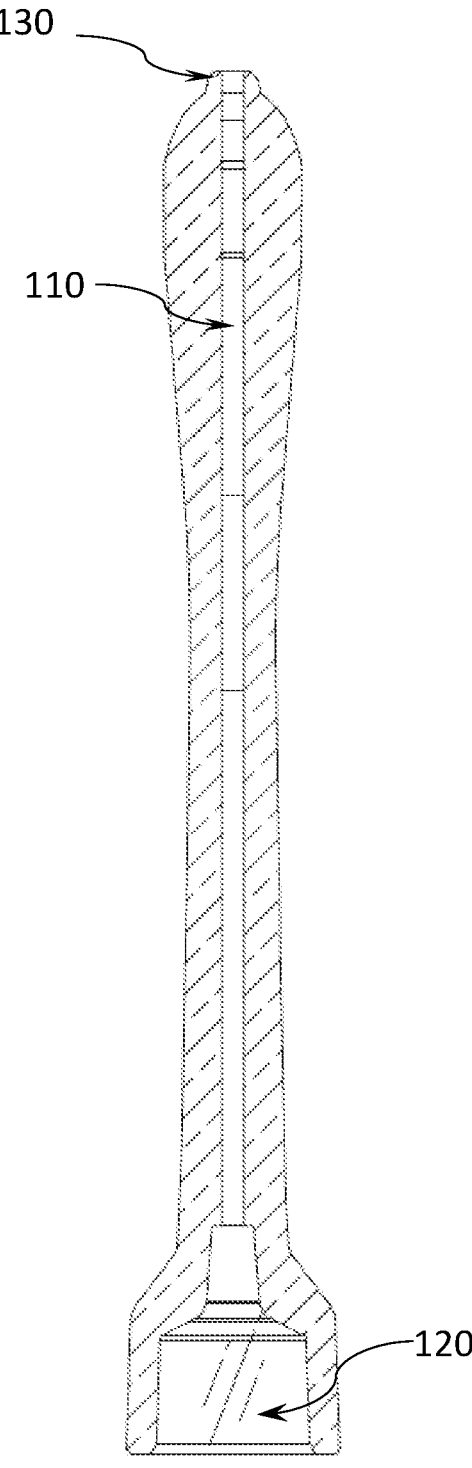
FIG. 3 is a cross-sectional view of the device shown in FIG. 2 taken along the line 8-8', according to an exemplary embodiment of the present invention.
Figure 4:
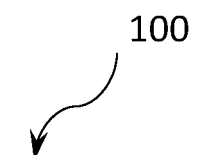
FIG. 4 is a bottom and side perspective view of the device, according to an exemplary embodiment of the present invention.
Figure 4:
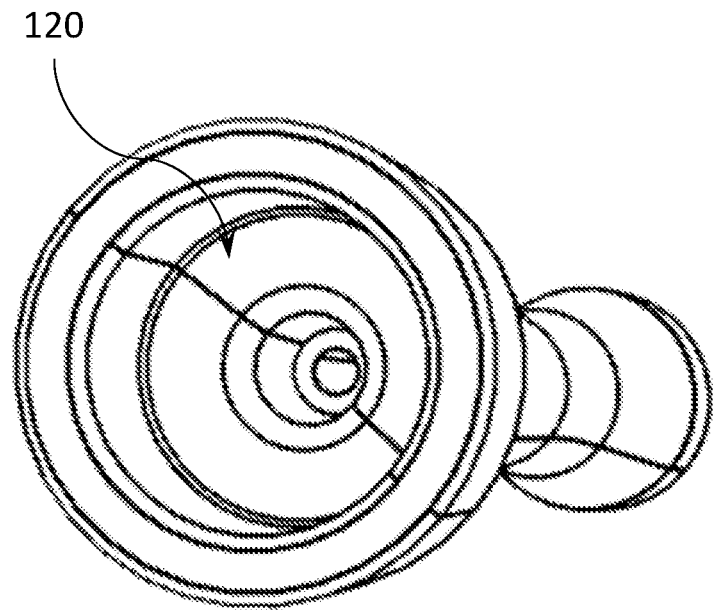

The hub can be more clearly seen in FIGS. 3 and 4, and the hub is shaped such that the tip of the syringe can fit into the hub. In case, the tip of the syringe has any fastening mechanism, a suitable fastening mechanism can also be provided in the hub that allows for the fastening of the syringe to the hub.

Figure 5:
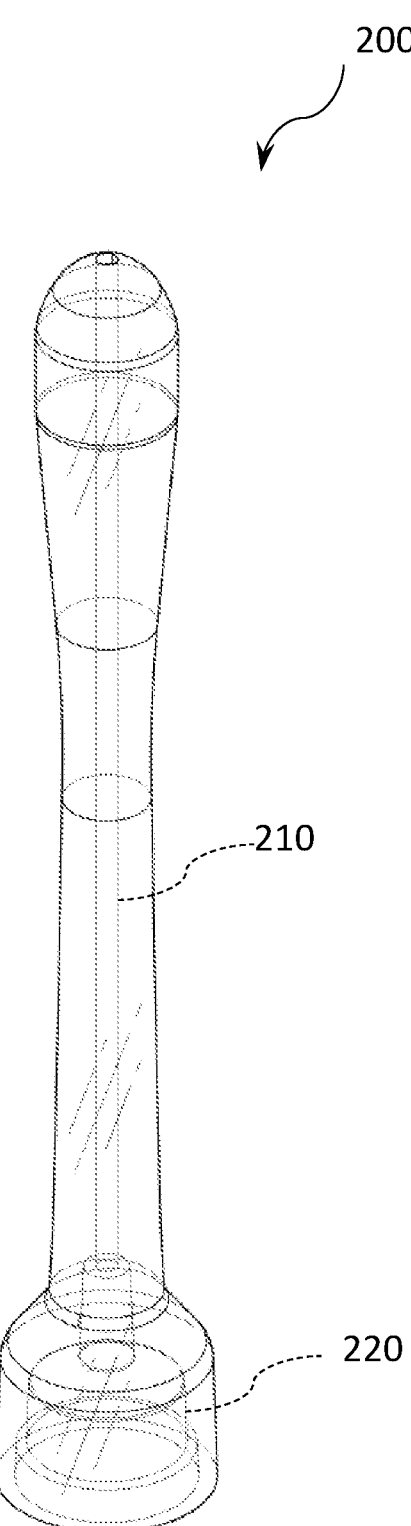
FIG. 5 is a perspective view of another embodiment of the device, according to the present invention.

A small protruding tip 130 can also be seen in FIG. 1 on the end of the body 105 and at the opening of the channel 110. The tip 130 of the device 100 makes it easier for the device 100 to reach a bottom corner of a cup containing the sperm or lubricant, allowing any remaining amount of the sperms or lubricants in the container to be sucked in. This minimizes the wastage of the sperms. Moreover, tip 130 can make the ejection of the sperms or lubricants from the channel into the vagina more focused. However, the protruding tip 130 can be optional. FIG. 5 shows device 200 having a channel 210 and a hub 220 which is similar to device 100 except the protruding tip 130 is omitted in FIG. 5.

The disclosed device can be made from semi-rigid material, such as silicone. The semi-rigidity of the device can allow the device to be maneuvered into the vagina and at the same time, the flexibility can allow it to bend within the various curves and shapes of the vagina, gliding into the vagina with minimum resistance and repulsion during the insertion. The oval proximal portion and narrow tubular middle portion make the steering of the device into the vagina easier and more comfortable.

The disclosed device with a syringe can be provided in suitable sterile packaging. For use, the device and the syringe can be taken out from the packaging. While the sperms can be collected in a container, the container can also be provided in the packaging; the syringe and the device can be assembled. Thereafter, the tip of the device can be dipped into the sperms contained in the container. The plunger of the syringe can then be pulled to draw the sperms into the channel of the device. The sperms can be collected into the barrel of the syringe. Any remaining amount of the sperms in the container can be carefully drawn into the channel. Once the sperms could be drawn into the channel and the syringe, the device at the tip can be inserted into the vagina. The device can be gently steered into the vagina with slight force, such that at least the proximal portion of the device is well within the vagina. Now the plunger of the syringe can be pushed to eject the sperms into the vagina all at once, allowing the sperms to travel faster towards the uterus.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A device to aid insemination process, the device comprises:
    an elongated tubular body that has a proximal portion, a middle portion, and a distal portion, the proximal portion is of an oval shape, the middle portion is of a narrow tubular shape, and the distal portion is configured as a hub to sealably receive a tip of a syringe, the hub comprises a broad pocket configured to receive an end portion of a barrel of the syringe and a tubular groove extending from the broad pocket is configured to receive a hub of the syringe, wherein a diameter of the proximal portion increases from the middle portion to a maximum diameter and then decreases, wherein the maximum diameter of the proximal portion is larger than a maximum diameter of the middle portion; and a hollow central channel extends throughout a length of the elongated tubular body, wherein the hollow central channel at one end opens at a tip of the elongated tubular body and another end of the hollow central channel opens at the hub, wherein the device is semi-rigid such that it can bend within various curves and shapes of a vagina.

2. The device according to claim 1, wherein the device further comprises a protruding tip at the tip of the elongated tubular body along with the opening of the hollow central channel.

3. The device according to claim 1, wherein the device is made from silicone.

4. The device according to claim 1, wherein the device further comprises the syringe, wherein the tip of the syringe is configured to be removably coupled to the hub.

5. The device according to claim 4, wherein the tip of the syringe frictionally fits into the hub.

6. The device according to claim 4, wherein the tip of the syringe and the hub have an interlocking fastening mechanism for securing the tip of the syringe into the hub.

7. A method to aid insemination process, the method comprising the steps of:

providing a device comprising:

an elongated tubular body that has a proximal portion, a middle portion, and a distal portion, the proximal portion is of an oval shape, the middle portion is of a narrow tubular shape, and the distal portion is configured as a hub to sealably receive a tip of a syringe, the hub comprises a broad pocket configured to receive an end portion of a barrel of the syringe and a tubular groove extending from the broad pocket is configured to receive a hub of the syringe, wherein a diameter of the proximal portion increases from the middle portion to a maximum diameter and then decreases, wherein the maximum diameter of the proximal portion is larger than a maximum diameter of the middle portion, and a hollow central channel that extends throughout a length of the elongated tubular body, wherein the hollow central channel at one end opens at a tip of the elongated tubular body and another end of the hollow central channel opens at the hub, wherein the device is semi-rigid such that it can bend within the various curves and shapes of a vagina;

coupling the tip of the syringe to the hub;

upon coupling, drawing using the syringe, fluid from a container into the hollow central channel and a barrel of the syringe;

inserting the device into vagina of a patient in need of getting pregnant; and pushing a plunger of the syringe to eject the fluid through the hollow central channel.

8. The method according to claim 7, wherein the device further comprises a protruding tip at the tip of the elongated tubular body along with the opening of the hollow central channel.

9. The method according to claim 7, wherein the device is made from silicone.

10. The method according to claim 7, wherein the device further comprises the syringe, wherein the tip of the syringe is configured to be removably coupled to the hub.

11. The method according to claim 10, wherein the tip of the syringe frictionally fits into the hub.

12. The method according to claim 10, wherein the tip of the syringe and the hub have an interlocking fastening mechanism for securing the tip of the syringe into the hub.

* * * * *